(12) United States Patent
Heethaar et al.

(10) Patent No.: US 6,560,481 B1
(45) Date of Patent: May 6, 2003

(54) METHOD FOR THE IN-VIVO NON-INVASIVE MEASUREMENT OF A BIOLOGICAL PARAMETER

(75) Inventors: Robert Martin Heethaar, Cothen (NL); Alexander Emanuel Hoetink, Amsterdam (NL)

(73) Assignee: A. J. Van Liebergen Holding, B.V., Leusden (NL)

( * ) Notice: Subject to any disclaimer, the term of this patent is extended or adjusted under 35 U.S.C. 154(b) by 0 days.

(21) Appl. No.: 09/882,862

(22) Filed: Jun. 15, 2001

(51) Int. Cl.[7] ................................. A61B 5/02
(52) U.S. Cl. ........................... 600/547; 600/506
(58) Field of Search .................. 600/547, 536, 600/506

(56) References Cited

U.S. PATENT DOCUMENTS 4,450,527 A * 5/1984 Sramek ................. 364/415
5,529,072 A * 6/1996 Sramek ................. 128/693

OTHER PUBLICATIONS

Raaijmakers, E., et al., "Thoracic Geometry and Its Relation to Electrical Current Distribution: Consequences for Electrode Placement in Electrical Impedance Cardiography," *Medical & Biological Engineering & Computing* (Sep. 1998) pp 592–597.

* cited by examiner

Primary Examiner—Kevin Lee
(74) Attorney, Agent, or Firm—Jeffrey D. Myers

(57) ABSTRACT

Method for the in-vivo non-invasive measurement of a biological parameter of a person employing the placement of current injecting electrodes on the person's body, and the placement of measurement electrodes on said person's body between the current injecting electrodes, feeding a measuring current through the current injecting electrodes and the body connected thereto, and measuring a voltage over the measurement electrodes indicative for the biological paramater, whereby a first measurement electrode is placed near a clavicle of the person and a second measurement electrode is placed at the person's left hand side below the sternum.

3 Claims, 2 Drawing Sheets

BOX PLOTS OF THE OBSERVED VALUES FOR $Z_0$, $dZ/dt_{min}$, $T_{LVE}$ AND CALCULATED $SV_K$ FOR EACH ELECTRODE ARRANGEMENT IN FIGURE 1. THE CIRCLES REPRESENT OUTLIERS.

BOX PLOTS OF THE OBSERVED VALUES FOR $Z_0$, $dZ/dt_{min}$, $T_{LVE}$ AND CALCULATED $SV_K$ FOR EACH ELECTRODE ARRANGEMENT IN FIGURE 1. THE CIRCLES REPRESENT OUTLIERS.

METHOD FOR THE IN-VIVO NON-INVASIVE MEASUREMENT OF A BIOLOGICAL PARAMETER

BACKGROUND OF THE INVENTION

The invention relates to a method for the in-vivo non-invasive measurement of a biological parameter of a person employing the placement of current injecting electrodes on the person's body, and the placement of measurement electrodes on said person's body between the current injecting electrodes, feeding a measuring current through the current injecting electrodes and the body connected thereto, and measuring a voltage over the measurement electrodes indicative for the biological parameter.

Such a method is known from the article "Optimalisation of the spot electrode array in impedance cardiography, by Woltjer H H et al, Medical & Biological Engineering & Computing 1996, (34) pages 84–87. In said citation it is proposed to apply an arrangement on the persons body, employing nine spot electrodes of which five are current injecting electrodes and four are voltage pick-up electrodes.

SUMMARY OF THE INVENTION

It is the object of the invention to reduce the number of electrodes that are to be used in the measurement method according to the preamble, whilst maintaining the reliability and repeatability of the known method. Obviously reducing the number of electrodes needed in this method is more comfortable for the patient and more practical for medical personnel, especially in the intensive care unit and after extensive surgery.

The object and further advantages of the invention are realised in the method specified in the appended claims.

In a first aspect of the invention a first measurement electrode is placed near a clavicle of the person and a second measurement electrode is placed at the person's left-hand side below the sternum.

Preferably the first measurement electrode is placed in the triangular clavicular space between the person's neck and shoulder.

It has been found advantageous that the lowest current injecting electrode is placed at least 6 cm below the second measurement electrode and preferably this lowest current injecting electrode is placed 15–20 cm below the second measurement electrode.

BRIEF DESCRIPTION OF THE DRAWINGS

The invention will now be further elucidated with reference to an example from field experience, and with reference to the drawing showing.

Figure 1:
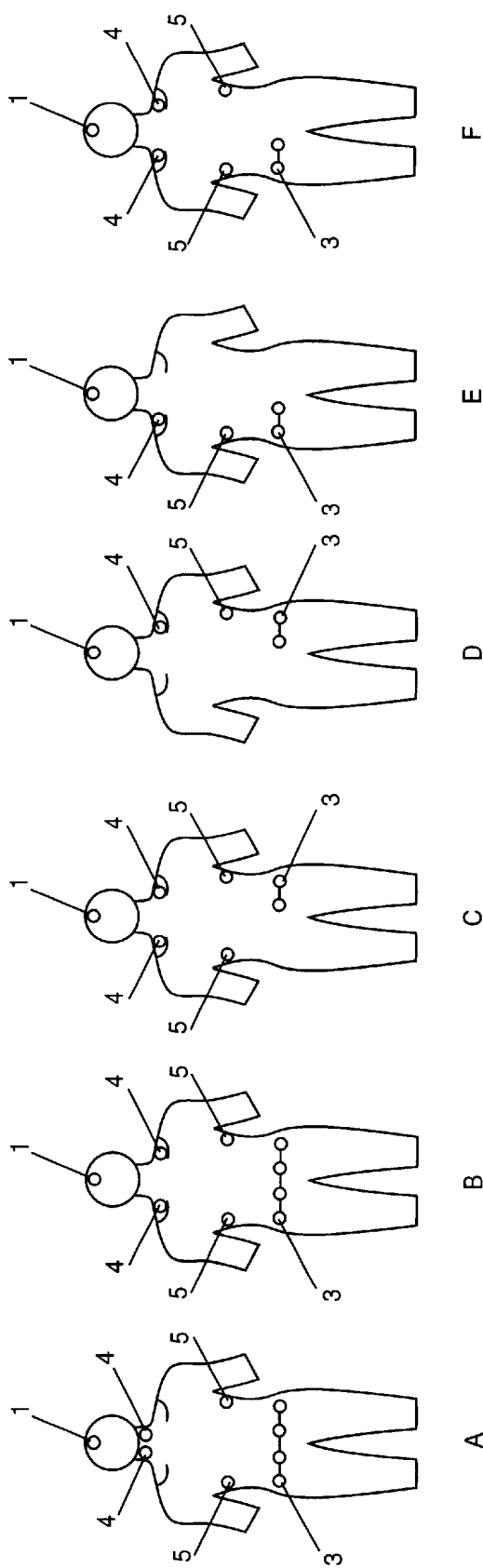
in FIG. 1: the investigated electrode arrangements, and
in FIG. 2: measurement results.

DESCRIPTION OF THE PREFERRED EMBODIMENTS (BEST MODES FOR CARRYING OUT THE INVENTION)

Field Experiments

The field experiment was conducted with 15 healthy subjects, 6 females and 9 males. Six electrode arrangements a–f were used to obtain a thoracic bio-impedance signal (see FIG. 1). All arrangements place the upper current injecting spot electrode on the forehead as indicated with reference numeral 1. The lower current injecting electrodes 3 are placed at least 6 cm, preferably 15–20 cm below the lower voltage pickup electrodes 5. Arrangement a places the upper voltage pickup electrodes 4 in the neck, at least 5 cm above the clavicle. All other arrangements place the upper voltage pickup electrodes 5 as close as possible to the clavicles at the lateral aspect of the base of the neck. The lower voltage pickup electrodes are placed at the crossing of the transverse plane at the xiphoid process and the mid-axillary line. The arrangements were specifically chosen for the following reasons:

Arrangement a is known from the article "*Thoracic geometry and its relation to electrical current distribution: Consequences for electrode placement in electrical impedance cardiography*", Medical & Biological Engineering & Computing, 36 592–597, by Raaijmakers et al. (1998), while arrangement b is a modification of arrangement a, eliminating the influence of the neck.

Arrangements c and f differ from arrangement b only in the location of the current injecting electrodes 3. Thus, comparing arrangement c and arrangement b, and comparing arrangement f and arrangement b will indicate whether the number of lower current injecting electrodes 3 can be reduced from four to two.

Arrangement d differs from arrangement c in the number of voltage pickup electrodes, while the current injecting electrode arrangements 1,3 are the same. Likewise, arrangement e differs from arrangement f only in the number of voltage pickup electrodes 4,5, but now the voltage pickup 5 and current injecting electrodes 3 are located at the right-hand side of the thorax. Consequently, comparing arrangement c and arrangement d, and comparing arrangement e and arrangement f will indicate whether the voltage pickup electrodes 4, 5 can be reduced from four to two. Furthermore, comparing arrangement d and arrangement e will indicate whether two voltage pickup 4, 5 and current injecting electrodes 3 applied on the left-hand side of the thorax will yield the same result as an arrangement placing these electrodes on the right-hand side of the thorax.

The bio-impedance signal measured is the stroke volume of the heart as estimated according to the so-called Kubicek estimator as described in the article "*Development and evaluation of an impedance cardiac output system*", By Kubicek et al published in Aerospace Medicine, 1966, volume 37, pages 1208–1212.

The variables obtained from the bio-impedance signal were:

$Z_0$ mean of the measured impedance between the voltage pickup electrodes ($\Omega$), $\Delta_Z$ total measured impedance minus $Z_0$ ($\Omega$), $dZ/dt_{min}$ peak value of negative deflection of the first derivative of $\Delta_Z$ ($\Omega$), $T_{LVE}$ left ventricular ejection time (s)

The signals were ensemble averaged with reference to $dZ/dt_{min}$ (at least 30 heartbeats) to remove the effects of respiration. To determine the influence of variations of the observed variables on a stroke volume estimator, the above mentioned Kubicek estimator was used:

$$SV_K = -\frac{\rho l_e^2}{Z_0^2} dZ/dt_{min} T_{LVE}$$

Where $SV_K$ (ml) is the stroke volume, $\rho$ is the resistivity of blood (and taken as 135 $\Omega$cm) and $l_e$ (cm) is the distance between the voltage pickup electrodes 4 and 5. The directly measured values of the variables, using the different arrangements a–f, and the corresponding calculated values of $SV_K$ were compared. To this end an analysis of variance was used, although the order in which the electrode arrangements were measured was not randomized (they were measured in order of increasing arrangement number a–f, see FIG. 1).

Figure 2:
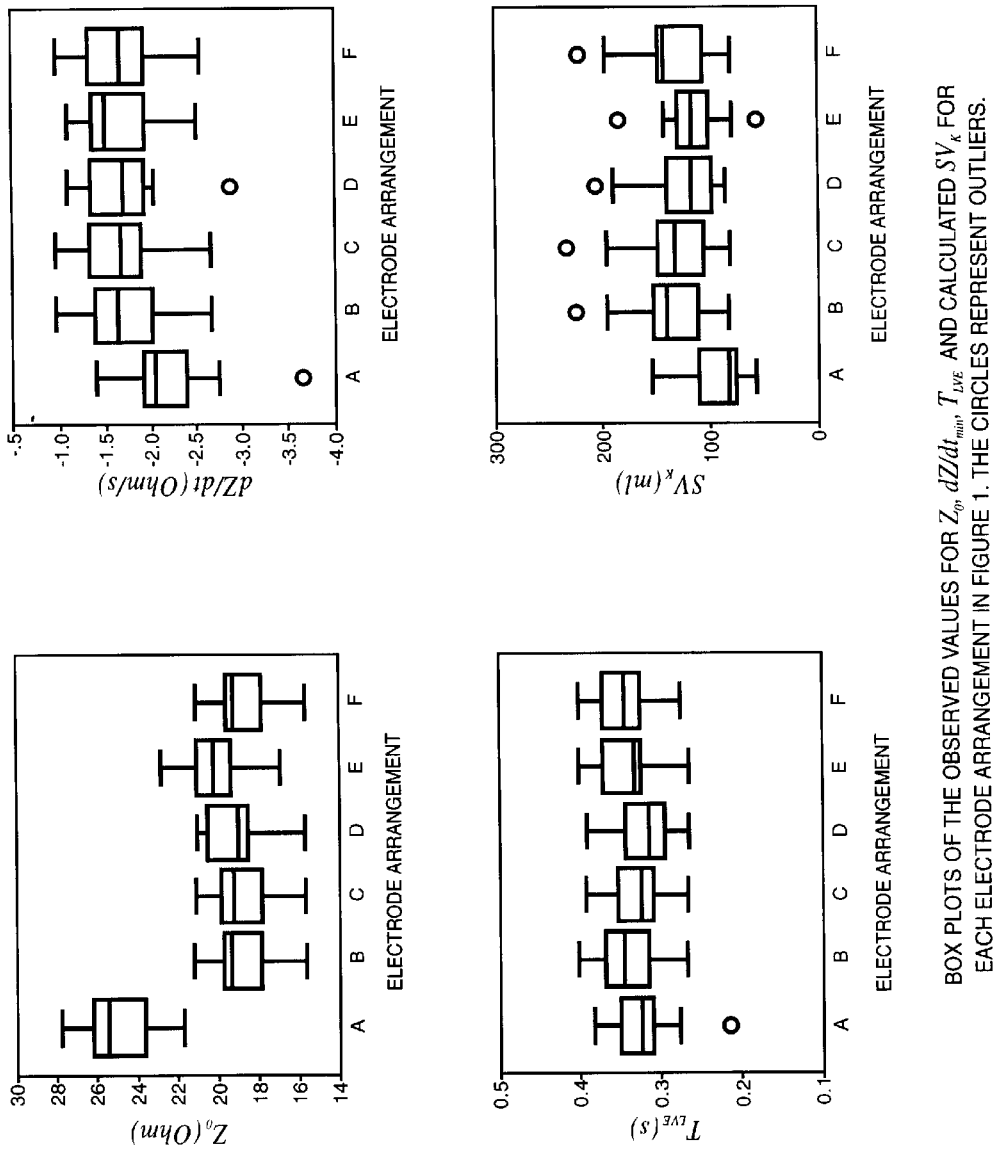

FIG. 2 shows the box plots for the observed values of $Z_0$, $dZ/dt_{min}$, $T_{LVE}$ and $SV_K$, in all subjects against electrode arrangement a–f. A box plot as shown in FIG. 2 is a summary plot based on the median, quartiles and extreme values. The box represents the interquartile range which contains 50% of the values. The whiskers are lines that extend from the box to the highest and lowest values, excluding outliers (cases with values between 1.5 and 3 box lengths from the upper or lower edge of the box). A line across the box indicates the median.

In the table I shown below the results of a comparison between the different arrangements a–f according to FIG. 1 are shown with respect to the directly measured variables and $SV_K$, respectively. The first column gives the arrangements that were compared. Columns two, three, four and five present the relative differences (%) between the values of the treatment means of the compared arrangements, respectively. For example, the estimated value of the treatment mean of $Z_0$ for arrangement a is 33% higher than the estimated value of the treatment mean of $Z_0$ for arrangement b.

TABLE I

| El.Arr. | $Z_O$ | $dZ/dt_{min}$ | $T_{LVE}$ | $SV_K$ | Consequently |
|---------|-------|---------------|-----------|--------|--------------|
| a-b | 33% | 28% | −4.8% | −31% | arr. a differs from all other |
| c-b | −0.1% | −1.7% | −1.7% | 2.5% | Lower current inj. |
| f-b | −0.4% | −3.8% | 1.6% | −1.3% | electrodes can be reduced from 4 to 2 |
| d-b | 2.1% | −0.2% | −4.3% | −8.1% | 2 voltage pickup |
| d-c | 2.2% | 1.5% | −2.6% | −5.7% | electrodes can be used on left-hand side |
| e-b | 6.9% | −3.5% | 0.6% | −14% | 2 voltage pickup |
| e-f | 7.4% | 0.2% | −0.9% | −13% | electrodes on right-hand |
| e-d | 4.7% | −3.4% | −5.1% | −6.7% | side give significant differences |

Arrangement a yields significantly different results compared with all other arrangements b–f for $Z_0$, $dZ/dt_{min}$, and $SV_K$, but not for $T_{LVE}$. For the sake of economy, only the results of pair wise comparison between arrangement a and b are presented. Comparing arrangement b and arrangement c, b and d, and b and f, respectively, no significant differences are found for the values of all observed variables and $SV_K$. This indicates that the number of current injecting electrodes 1,3 can be reduced from 5 to 3 and that the number of voltage pickup electrodes can be reduced from 4 to 2, provided that they are placed on the left-hand side of the thorax. Comparison of arrangement c and d again yields no significant differences for the values of all observed variables and $SV_K$. Comparing arrangements e and f shows that significant differences exist between the values of $Z_0$ and $SV_K$. The same holds when arrangements b and e are compared. Arrangements d and e yield significant differences for the value of $Z_0$, but not for the calculated value of $SV_K$. This study shows that reducing the number of current injecting spot electrodes from five to three and the voltage pickup spot electrodes from four to two electrodes does not give significant differences in the values of the observed variables and $SV_K$, provided that the electrodes are placed on the left-hand side of the thorax, and that the minimum distance between current injecting 3 and voltage pickup electrodes 5 exceeds 6, preferably 15 cm. Furthermore, it is expected that, the two lower current injecting electrodes 3 can be combined into a single large one.

The results further show that when the current injecting and the voltage pickup electrodes are placed at the right-hand side of the thorax, significant differences are found in the values of $Z_0$ and $SV_K$.

What is claimed is:

1. A method for the in-vivo non-invasive measurement of a biological parameter of a person, the method comprising the steps of placing current injecting electrodes on the person's body, placing measurement electrodes on said person's body between the current injecting electrodes, feeding a measuring current through the current injecting electrodes and the body connected thereto, and measuring a voltage over the measurement electrodes indicative for the biological parameter, wherein a first measurement electrode is placed in the person's triangular clavicular space between the person's neck and shoulder and a second measurement electrode is placed at the person's left hand side below the person's sternum.

2. The method according to claim 1, wherein a lowest current injecting electrode is placed at least 6 cm below the second measurement electrode.

3. The method according to claim 2, wherein a lowest current injecting electrode is placed 15–20 cm below the second measurement electrode.

* * * * *